(12) United States Patent
Pernot et al.

(10) Patent No.: US 11,571,230 B2
(45) Date of Patent: Feb. 7, 2023

(54) ULTRASONIC PROCESSING APPARATUS COMPRISING MEANS FOR IMAGING CAVITATION BUBBLES

(71) Applicants: CARDIAWAVE SA, Paris (FR); INSTITUT NATIONAL DE LA SANTE ET DE LA RECHERCHE MEDICALE, Paris (FR); CENTRE NATIONAL DE LA RECHERCHE SCIENTIFIQUE, Paris (FR); ECOLE SUPERIEURE DE PHYSIQUE ET DE CHIMIE INDUSTRIELLES DE LA VILLE DE PARIS, Paris (FR)

(72) Inventors: Mathieu Pernot, Paris (FR); Daniel Suarez, Paris (FR)

(73) Assignees: CARDIAWAVE SA, Paris (FR); INSTITUT NATIONAL DE LA SANTE ET DE LA RECHERCHE MEDICALE, Paris (FR); CENTRE NATIONAL DE LA RECHERCHE SCIENTIFIQUE, Paris (FR); ECOLE SUPERIEURE DE PHYSIQUE ET DE CHIMIE INDUSTRIELLES DE LA VILLE DE PARIS, Paris (FR)

(*) Notice: Subject to any disclaimer, the term of this patent is extended or adjusted under 35 U.S.C. 154(b) by 18 days.

(21) Appl. No.: 17/057,942

(22) PCT Filed: May 24, 2019

(86) PCT No.: PCT/EP2019/063455
§ 371 (c)(1),
(2) Date: Nov. 23, 2020

(87) PCT Pub. No.: WO2019/224350
PCT Pub. Date: Nov. 28, 2019

(65) Prior Publication Data
US 2021/0212709 A1 Jul. 15, 2021

(30) Foreign Application Priority Data
May 25, 2018 (FR) .................................. 1854428

(51) Int. Cl.
*A61B 17/225* (2006.01)
*A61B 8/14* (2006.01)
(Continued)

(52) U.S. Cl.
CPC ............ *A61B 17/2258* (2013.01); *A61B 8/14* (2013.01); *A61B 8/5207* (2013.01);
(Continued)

(58) Field of Classification Search
None
See application file for complete search history.

(56) References Cited

U.S. PATENT DOCUMENTS

| 2011/0054315 A1 | 3/2011 | Roberts et al. |
| 2016/0157828 A1* | 6/2016 | Sumi ...................... G01N 29/46 702/189 |
| 2018/0169444 A1* | 6/2018 | Averkiou ................ A61N 7/02 |

FOREIGN PATENT DOCUMENTS

| EP | 3236467 A1 | 10/2017 |
| WO | WO 2016/156989 A1 | 10/2016 |
| WO | WO 2017/182655 A1 | 10/2017 |

OTHER PUBLICATIONS

Arnal, B., et al., "In vivo real-time cavitation imaging in moving organs", Phys Med Biol., Jan. 10, 2017, vol. 62, No. 3, pp. 843-857.
(Continued)

*Primary Examiner* — Shahdeep Mohammed
(74) *Attorney, Agent, or Firm* — BakerHostetler (57) ABSTRACT

An ultrasonic processing apparatus is provided. The ultrasonic processing apparatus comprises an ultrasonic therapy transducer (ATA) adapted to generate focused ultrasonic waves; an ultrasonic imaging transducer (UID) connected to
(Continued)

the ultrasonic therapy transducer; and an electronic system configured to control the ultrasonic therapy transducer so as to emit a pulse train of ultrasonic waves generating a cloud of cavitation bubbles (BC); control the ultrasonic imaging transducer so as to acquire at least one image of the region to be processed; acquire a plurality of echo signals of ultrasonic wave pulses emitted by the ultrasonic therapy transducer captured by the ultrasonic imaging transducer; process the plurality of echo signals so as to reconstruct an image of the cloud of cavitation bubbles; and display said image of the cloud of cavitation bubbles superposed on said image of the region to be processed. The processing includes spatio-temporal filtering.

20 Claims, 3 Drawing Sheets

(51) Int. Cl.
  *A61B 8/08*      (2006.01)
  *A61B 8/00*      (2006.01)
  *A61B 17/00*     (2006.01)
(52) U.S. Cl.
  CPC .............. *A61B 8/5269* (2013.01); *A61B 8/54* (2013.01); *A61B 2017/00106* (2013.01); *A61B 2017/00172* (2013.01)

(56) References Cited

OTHER PUBLICATIONS

Bader, Kenneth, et al., "Post Hoc Analysis of Passive Cavitation Imaging for Classification of Histotripsy-Induced Liquefaction in Vitro", IEEE Transactions on Medical Imaging, Aug. 2017, 11 pages.

Boulos, P., et al., "Passive cavitation imaging using an open ultrasonic system and time reversal reconstruction", 22ème Congrès Français de Mécanique Lyon, Aug. 28, 2015, 7 pages.

Coviello, Christian, et al., "Passive acoustic mapping utilizing optimal beamforming in ultrasound therapy monitoring", The Journal of the Acoustical Society of America, May 2015, vol. 137, No. 5, pp. 2573-2585.

Haworth, Kevin J., et al., "Quantitative Frequency-Domain Passive Cavitation Imaging", IEEE Transactions on Ultrasonics, Ferroelectrics, and Frequency Control, Jan. 2017, vol. 64, No. 1., pp. 177-191.

Institut National De La Propriété Industrielle, Preliminary Search Report and Written Opinion received for French Application No. FR1854428, dated Feb. 21, 2019, 7 pages, Republic of France.

International Searching Authority, International Search Report (ISR) and Written Opinion received for International Application No. PCT/EP2019/063455, dated Jul. 4, 2019, 12 pages, European Patent Office, Netherlands.

* cited by examiner

ULTRASONIC PROCESSING APPARATUS COMPRISING MEANS FOR IMAGING CAVITATION BUBBLES

CROSS-REFERENCE TO RELATED APPLICATIONS

The present application is a national phase entry of PCT/EP2019/063455, filed on May 24, 2019, which claims the benefit of priority of French Patent Application No. 1854428, filed on May 25, 2018, the entire contents of which are hereby incorporated by reference in their entirety for all purposes.

FIELD

The invention relates to an apparatus for providing treatment by ultrasound, of a human or animal body. It is in particular applicable to treatment by high-intensity focused ultrasound (HIFU), histotripsy, lithotripsy, thrombotripsy, etc., of moving organs, i.e. typically abdominal and thoracic organs.

BACKGROUND

Histotripsy is a technique for mechanically fragmenting tissues by means of focused ultrasonic pulses that generate clouds of cavitation bubbles (also called "cavitation clouds" for the sake of simplicity). The use of histotripsy to treat various pathologies is a promising approach that could replace high-risk surgery. The cavitation allows undesirable tissues in a highly controlled focal region to be destroyed noninvasively and without thermal effects. However, the human body is a very heterogeneous medium and the fact that the therapy takes place inside the body with no direct visual feedback makes it crucial to precisely monitor the cavitation region. In particular, in cardiac applications, the rib cage may cause substantial aberrations in the therapeutic path of the ultrasound.

Similar considerations apply to techniques that are conceptually similar to histotripsy, such as lithotripsy (fragmentation of kidney stones) and thrombotripsy (fragmentation of blood clots), or even to the field of therapy by high-intensity focused ultrasound.

Analysis of the harmonics of the frequency of backscattered ultrasound echoes allows the cavitation to be detected passively, but does not allow the cloud of bubbles to be precisely located.

It is possible to use conventional B-mode ultrasonic imaging techniques that allow the cavitation effect and the anatomical structures being treated to be viewed in real-time. This approach is however not entirely satisfactory. Specifically, since the bubbles are generated within heterogeneous biological tissues, their echoes may be difficult to detect among all of the echoes from the tissue. The identification of bubbles therefore remains very subjective, non-quantitative, and the definition of the outlines of the cavitation cloud is problematic.

Article [1] teaches that a better discrimination of the cavitation bubbles may be obtained by employing a parallel (or "ultra-rapid") ultrasonic imaging technique associated with spatio-temporal filtering. However, this approach proves not to be very suitable in the case where the treated tissues are constantly moving, such as for example in the case of the heart, the liver or the kidneys. Specifically, the ultrasonic waves used for the imaging insonify all of the region of interest (or even a region larger than the region of interest), and their echo signals are very sensitive to any spatio-temporal variations that occur in this region, and not solely those due to the cavitation. This is acceptable when the tissues are static or quasi-static but, in the presence of moving tissues, spatio-temporal filtering becomes a much less effective way of identifying the echo signals coming from the cavitation bubbles. However, it is precisely in the latter case that is particularly important to be able to view the cavitation cloud and its position with respect to the tissues with precision.

Passive detecting methods have also been used to estimate the position of cavitation bubbles. For example:

[2] describes a passive method for acoustically mapping bubbles generated by a thermal-ablation therapy transducer. This method allows the bubbles produced by continuous-wave emissions or emissions of wave trains of long duration (several hundred oscillations) to be mapped. Because of the duration of the wave trains, it is not possible to precisely identify the position of the cloud of bubbles. [2] proposes a method for computing a map of backscattered energy with a resolution equivalent to the wavelength used, but this does not allow the boundaries of the cloud to be precisely identified.

[3] describes an alternative method to [2] for solving the same problem of monitoring continuous emissions.

[4] describes the application of the method [2] to histotripsy without particular modifications.

[5] describes a method that applies time reversal to the ultrasonic pulses. As in references [2], [3] and [4], this method uses long pulses and does not allow the boundaries of the cloud of cavitation bubbles to be precisely identified.

SUMMARY

The invention aims to overcome the aforementioned drawbacks of the prior art, and more particularly to provide an imaging technique that allows the cavitation cloud to be precisely located and segmented, including during the treatment of moving tissues.

According to the invention, this aim is achieved by associating active ultrasonic imaging of the tissues, synchronous passive cavitation imaging and spatio-temporal filtering (for example, singular value decomposition). The synchronous passive imaging is based on the reconstruction of the echoes of the interaction of a therapeutic ultrasonic beam with the medium, synchronized with the emission sequence of the therapeutic pulses. It is robust to tissue movement and hence a good performance may be obtained even when the imaged tissue is moving.

The technique of the invention allows the cloud of cavitation bubbles to be located with a spatial resolution that increases as the duration of the ultrasonic pulses used for the imaging, i.e. the ultrasonic therapy pulses, decreases. Thus, preferably, these pulses will have a duration comprised between 0.1 μs and 50 μs (this, in any case, being desirable for focused therapeutic pulses). The imaging methods described in references [2] to [5] would gain nothing from using short pulses.

The application of spatio-temporal filtering to passive cavitation imaging has already been suggested in document [6], but in a completely different context, that of opening the blood-brain barrier by ultrasound. This technique uses injected microbubbles and ultrasound of insufficient intensity to generate cavitation bubbles. Moreover, echoes are acquired through the skull, this making use of active ultrasonic techniques to image the treated tissues almost impossible.

One subject of the invention is therefore an apparatus for providing treatment with ultrasound, comprising:
- a therapy ultrasound transducer, suitable for generating focused ultrasonic waves;
- an imaging ultrasound transducer associated with the therapy ultrasound transducer; and
- an electronic system configured to:
  - control the therapy ultrasound transducer so as to emit a pulse train of ultrasonic waves of energy and with a duration suitable for causing the generation of a cloud of cavitation bubbles in the focal spot of the transducer when said focal spot is positioned inside a region to be treated of a human or animal body;
  - control the imaging ultrasound transducer so as to emit, between two ultrasonic-wave pulses emitted by the therapy ultrasound transducer, ultrasonic waves that are directed toward the region to be treated, to acquire echoes of said ultrasonic waves and to process them to reconstruct at least one image of the region to be treated;
  - acquire a plurality of echo signals of N>1 ultrasonic-wave pulses emitted by the therapy ultrasound transducer, said signals being captured by the imaging ultrasound transducer;
  - process the acquired signals using a beamforming algorithm, so as to form respective echo images, and using spatio-temporal filtering allowing components of said echo images that are representative of a backscatter of the ultrasonic-wave pulses from the cavitation bubbles to be extracted, separating them from components representative of a backscatter from tissues of the region to be treated, so as to reconstruct an image of the cloud of cavitation bubbles (these operations may be performed in this order or in the inverse order); and
  - display, superposed on said image of the region to be treated, said image of the cloud of cavitation bubbles.

According to particular embodiments of such an apparatus:
- Said electronic system may also be configured to, during the reconstruction of the image of the cloud of cavitation bubbles, introduce a compensation for a difference in propagation time of the ultrasonic waves between the therapy ultrasound transducer and the focal spot, and between the focal spot and the imaging ultrasound transducer.
- Said electronic system may also be configured to control the therapy ultrasound transducer so as to emit a train of ultrasonic-wave pulses with a duration comprised between 0.1 μs and 50 μs and preferably between 0.5 μs and 20 μs.
- N may be comprised between 2 and 10 000 and preferably between 2 and 1000.
- Said electronic system may also be configured to reconstruct the image of the cloud of cavitation bubbles by means of a parallel beamforming algorithm.
- Said electronic system and the therapy ultrasound transducer may be configured to emit ultrasonic-wave pulses with a duration comprised between 0.1 μs and 50 μs, with a central frequency comprised between 100 kHz and 5 MHz, at a repetition rate comprised between 1 and 1000 Hz.
- Said electronic system and the imaging ultrasound transducer may be configured to emit ultrasonic-wave pulses having a central frequency comprised between 2 and 15 MHz.
- Said electronic system may also be configured to perform said spatio-temporal filtering using singular value decomposition.
- The therapy ultrasound transducer and the imaging ultrasound transducer may be arranged coaxially.
- The apparatus may also comprise means for moving the focal spot of the ultrasonic-wave pulses emitted by the therapy ultrasound transducer in the treatment region.
- Said electronic system may also be configured to adjust a power level of the ultrasonic-wave pulses emitted by the therapy ultrasound transducer depending on the image of the cloud of cavitation bubbles.

BRIEF DESCRIPTION OF THE FIGURES

Other features, details and advantages of the invention will become apparent on reading the description given with reference to the appended drawings, which are given by way of example and which show, respectively.

DETAILED DESCRIPTION

Figure 1:
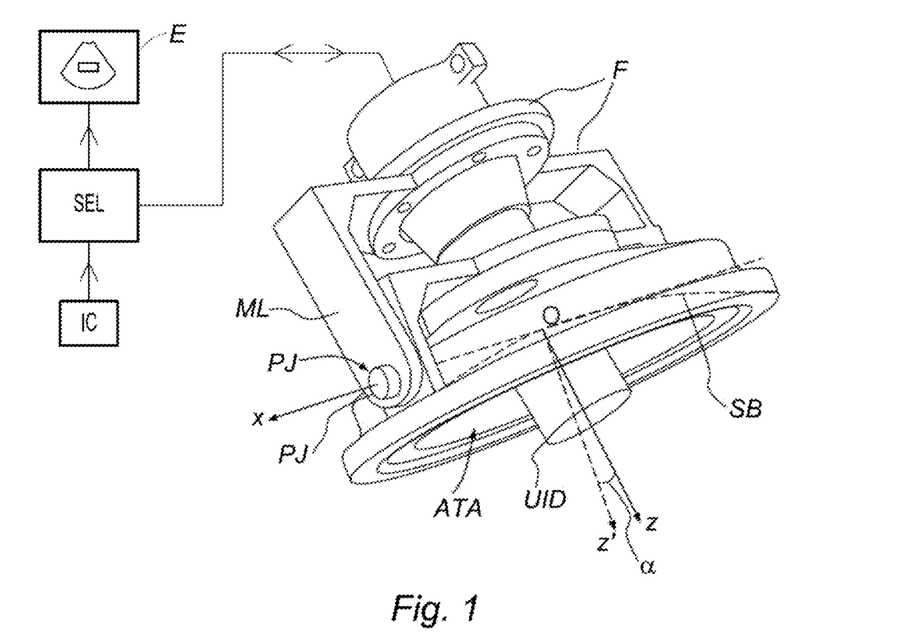
FIG. 1, an apparatus according to one embodiment of the invention.

The apparatus of FIG. 1 comprises an imaging ultrasound transducer UID arranged at the center of a therapy transducer ATA made up of a set of elementary transducers of annular shape, preferably in a number comprised between 5 and 20, said elementary transducers being arranged in an aligned and concentric way on a spherical bowl SB that focuses the ultrasonic waves. The imaging transducer UID is located at the center of the most internal ring of the therapy transducer.

The transducer UID comprises a plurality of ultrasound-detecting elements arranged in a one-dimensional (typically linear) or two-dimensional, periodic or aperiodic, array. It may for example be a question of a two-dimensional echographic probe comprising an array of 64 elements.

The imaging transducer UID is fastened to a scaffold F allowing it to be connected to a mechanical arm (not shown) connected to the therapy transducer by a mechanical link ML allowing a relative rotary movement about the Ox-axis (the reference PJ designates a pivot joint). Thus, it is possible to keep the orientation of the imaging transducer (along the Oz-axis) constant while modifying—by means of an electric motor (not shown)—the orientation of the therapy transducer (Oz'-axis), so as to allow a movement of the focal spot of the latter perpendicular to the Oz-axis. Furthermore, by finely controlling the offset between the control signals of the various elementary transducers, it is possible to modify the focal length of the therapy transducer, and therefore the position of the focal spot along the Oz'-axis. This allows a two-dimensional scan of a region to be treated to be carried out by hybrid mechanical and electronic means.

Variants are possible; for example, the mechanical link may also allow a rotation of the therapy transducer about a second axis, the Oy-axis, perpendicular both to Ox and to Oz.

The assembly of FIG. 1 is described in more detail in European patent application EP 3 236 467 A1. It is given merely by way of example, because many variants allow the invention to be implemented. For example, the scan of the region to be treated by the focal spot of the therapy transducer may also be achieved via purely mechanical means, or conversely purely electronic means (by virtue of the use of a matrix array of elementary transducers). It is moreover not essential for the imaging transducer to be coaxial to the therapy transducer, nor even mechanically linked to the latter: it is enough for their relative position to be controllable and for the focal spot of the ultrasonic therapy pulses to be located inside a region of observation of the imaging transducer.

Moreover, the imaging transducer may comprise a different number of elements, or be of biplanar or matrix-array type.

In any case, an electronic system SEL must be provided to control the imaging and therapy transducers so as to:
  generate focused ultrasonic-wave pulses suitable for inducing the formation of a cloud of cavitation bubbles;
  move the focal spot of these ultrasonic waves so as to scan a region to be treated;
  acquire and display echographic images of the region to be treated and of the cloud of cavitation bubbles, and display them on a screen E.

Figure 2:
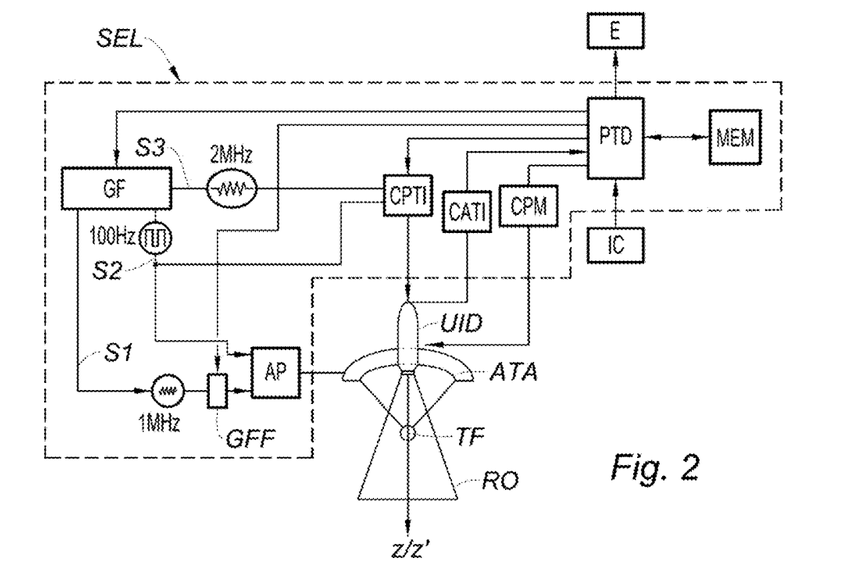
FIG. 2, a functional schematic of such an apparatus.

The electronic system SEL comprises both one or more processors that execute programs stored in a memory and analogue and/or digital electronic circuits that operate under the control of this or these processors. FIG. 2 shows a functional schematic. In this schematic, the reference PTD designates a data processor; generally, it may be a question of a board comprising a microprocessor or microcontroller, of a computer or of a more complex set of programmable digital electronic circuits. This data processor receives commands and/or parameters from a user, or operator, via an interface device IC (keyboard, computer mouse, etc.); controls the operation of a function generator GF, of a circuit CPTI for controlling the imaging transducer, of a beamforming circuit GFF and of a circuit CPM for controlling an electric motor; and processes the signals output from an acquiring circuit of the imaging transducer to reconstruct images that are displayed on the screen E.

The function generator GF generates a plurality of electronic signals that are delivered to other functional units of the electronic system. A first signal S1, for example a sinusoidal signal at a frequency of 1 MHz, is delivered to the beamforming circuit GFF which decomposes it into a plurality of individual signals of the same frequency having various phase shifts; these various signals are amplified by the power amplifier AP before being applied to the elementary transducers of the imaging transducer. As explained in detail in the European patent application EP 3 236 467 A1 cited above, the phase shifts introduced by the beamforming circuit GFF allow the focal length of the therapy transducer to be varied, and therefore the position of the focal spot TF of the ultrasound along the Oz'-axis to be varied. The function generator also generates a square-wave signal S2 of much lower frequency, for example 100 Hz, which activates and deactivates the power amplifier; in this way, the therapy transducer emits ultrasonic pulses ("therapy pulses") at a repetition rate of 100 Hz, the pulses for example having a duration of 8 µs.

The function generator GF also generates a high-frequency, for example 2 MHz, third signal S3 that is delivered with the signal S2 to the circuit CPTI for controlling the imaging transducer. This circuit controls the imaging transducer with a view to emitting low-intensity ultrasonic pulses in the intervals between the more intense pulses emitted by the therapy transducer. The propagation of these pulses defines an observation region RO that, in the case of a two-dimensional imaging transducer, has the shape of a trapezoid the height of which coincides with the Oz-axis.

The acquiring circuit CATI of the imaging transducer acquires echo signals that are detected by the imaging transducer UID, converts them into digital format and transmits them to the processor PTD that proceeds to process them. In a first time window that follows the emission of the ultrasonic therapy pulses and the duration of which (for example 250 µs) depends on the maximum depth of the focal spot TF, the imaging transducer detects the echoes of the therapy pulses, and therefore operates in passive mode; as will be explained in detail below, these echo signals allow the processor PTD to reconstruct images of the clouds of cavitation bubbles. In a second time window, which extends from the end of the first window to the emission of the following therapy pulse, the imaging transducer detects the echoes of the pulses that it itself emitted; this allows the processor PTD to reconstruct images of anatomic structures of the region to be treated using conventional active-ultrasonic-imaging techniques.

In the case of the pulses used for the active ultrasonic imaging, the same transducer serves as the ultrasound source and detector. Such is not the case with passive imaging, in which the ultrasonic pulses are emitted by the therapy transducer and the echoes thereof are detected by the imaging transducer. To be able to reconstruct the images of the cloud of cavitation bubbles, which images are acquired in passive mode, it is therefore necessary to know the difference between the "outward" travel time (from the therapy transducer to the focal spot) and the "return" travel time (from the focal spot to the imaging transducer). This may be obtained by computation, if the mechanical configuration of the apparatus is known with sufficient precision, but as a general rule it is preferred to carry out a calibration. To this end, it is possible to proceed in a number of different ways.
  Firstly, it is possible to place a hydrophone in correspondence with the focal spot and to measure the arrival times of the pulses emitted by the two transducers.
  Secondly, it is possible to place a reflector in correspondence with the focal spot and to use the imaging transducer in reception mode to measure the arrival times of the echoes of the pulses emitted by the imaging transducer itself and by the therapy transducer.

Hybrid approaches (use of the hydrophone to measure the "outward" travel time, and of the reflector to measure the "return" travel time) are also possible.

Whatever the method used, it is necessary to compute or measure the difference in travel time in correspondence with a plurality of points sampling the entire region to be treated.

Figure 3:
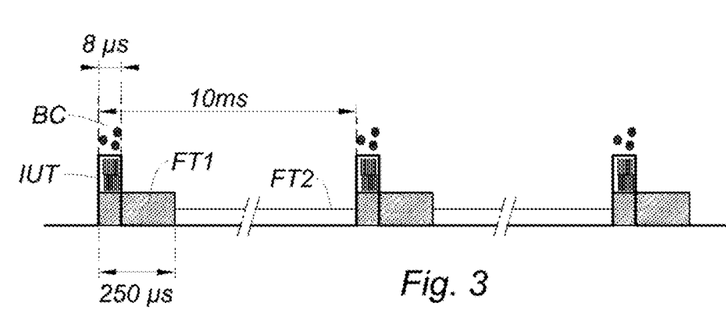
FIG. 3, a passive-imaging sequence according to one embodiment of the invention.

FIG. 3 is a timing diagram showing: the therapy pulses IUT, with a duration of 8 µs, emitted at a repetition rate of 100 Hz (periodicity of 10 ms), which generate a cloud of cavitation bubbles BC; the echo-acquisition first time windows FT1, which extend over 250 µs from the start of each therapy pulse; and the active-imaging second time windows FT2, which start at the end of each first window and extend up to the emission of the following therapy pulse.

The motor-controlling circuit CPM actuates an electric motor allowing the therapy transducer to be pivoted; it interacts with the beamforming circuit GFF to move the focal spot TF of the ultrasonic pulses in order to scan the region to be treated. It may be absent from embodiments in which the movement of the focal spot is achieved by purely electronic means (conversely, in other embodiments, the beamforming circuit may be omitted).

The various functional units described above (GF, CPTI, CATI, CPM, GFF, AP) do not necessarily correspond to physically separate components. For example, a single integrated circuit or circuit board may perform all or some of the functions of a plurality of these units. Conversely, the functions of a single block may be performed by a plurality of integrated circuits and/or circuit boards.

The characteristics of the pulses have been given by way of nonlimiting example. More generally, the imaging transducer may emit trains of pulses with a duration comprised typically between 0.1 µs and 50 µs (and preferably between 0.5 µs and 20 µs) at a central frequency comprised between 100 kHz and 5 MHz and at a repetition rate comprised between 1 and 1000 Hz, these pulses being suitable for generating, at the focal point, a peak positive pressure comprised between 50 MPa and 100 MPa and a peak negative pressure comprised between −2.5 MPa and −30 MPa. The imaging transducer generally operates at a frequency higher than that of the therapy transducer, typically a frequency comprised between 2 and 15 MHz; for example, it may emit ultrasonic waves at 2 MHz and, in reception mode, have a sampling frequency of 8 MHz.

As indicated above, an apparatus according to the invention acquires echographic images both in active mode, with a view to viewing the tissues of the region to be treated, and in passive mode, with a view to viewing the cloud of cavitation bubbles. The images are then fused in order to be displayed on a screen E, this allowing visual inspection of the position of the cavitation cloud with respect to the tissues. Preferably, these processing operations are performed in real time. The signals acquired in active mode also allow the energy absorbed by the cavitation to be estimated, and therefore the effectiveness (and/or the dangers) of the treatment in course to be evaluated.

The processor PTD may thus automatically control the intensity of the therapy pulse, and/or stop the processing in case of danger. For example, the processor may gradually increase the intensity of the ultrasonic pulses until a cavitation cloud having the desired properties (shape, dimensions, energy, etc.) is detected or, conversely, decrease the intensity while ensuring the persistence of the cavitation. The processor may also stop the processing when a desired dose has been deposited, or if the cavitation cloud is not detected in the desired location and therefore risks damaging tissues that are not to be treated.

The active-imaging signals may be processed in a way that is perfectly normal and that therefore does not need to be described in more detail. In contrast, in order to be able to effectively extract the images of the cavitation bubbles, the processor PTD must subject the signals acquired passively to specific processing. This processing comprises:
    acquiring echo signals of N, generally successive, therapy pulses, N typically being comprised between 2 and 10 000 and preferably between 2 and 1000;
    applying, to these echo signals, a beamforming reconstruction algorithm, to reconstruct N images; and
    applying spatio-temporal filtering to the images thus reconstructed in order to extract therefrom the contribution due to the cavitation bubbles.

The value of N must be strictly higher than 1 in order to allow the temporal filtering of the echo signals. The acceptable upper limit depends on the repetition rate of the ultrasonic pulses; with a high repetition rate, 1000 pulses per second, and N=10 000, one filtered image is obtained every 10 seconds, this being the minimum acceptable repetition rate for most surgical applications.

Image reconstruction is preferably achieved using a beamforming algorithm (not to be confused with the beamforming carried out with respect to the therapy pulses) of parallel—or ultra-rapid—type, known per se, but modified to include therein a compensation of the difference in propagation time on the outward and return paths (which is discussed above). This algorithm essentially consists of a coherent summation of the signals detected by the various elements of the imaging probe, these signals being shifted in time in such a manner as to compensate for the propagation delay of the ultrasonic waves on the outward and return paths (principle of electronic focusing). It will be understood that taking into account the spatial offset between the source of the ultrasound and the detector is necessary for effective focusing. In the spectral domain, the compensation of the offset is achieved via a shift in the phase of the signals.

The spatio-temporal filtering may use any blind source-separation algorithm allowing the echoes originating from cavitation bubbles to be differentiated from those issued, in particular, from tissues. It may for example be a question of a singular value decomposition, a (sparse or independent) principal-component analysis, or a non-negative matrix factorization, etc. Below, the case of singular vector decomposition will be considered.

Singular value decomposition (SVD) is a technique for decomposing matrices algebraically. It is suitable for application to local statistics of an image and concentrates a maximum energy into a small number of eigenvectors. It consists in factorizing a matrix $X_{m \times n}$ into the form where U is an orthogonal matrix of m×m size, V is an n×n orthogonal matrix and S is an m×n matrix the diagonal elements $\sigma_i$ of which are the singular values of X and the other elements are zeros. If n<m:

$$\begin{pmatrix} X_{11} & \cdots & X_{1n} \\ \vdots & \ddots & \vdots \\ X_{m1} & \cdots & X_{nm} \end{pmatrix} = \begin{pmatrix} U_{11} & \cdots & U_{1m} \\ \vdots & \ddots & \vdots \\ U_{mm} & \cdots & U_{mm} \end{pmatrix} \cdot \begin{pmatrix} \sigma_1 & \cdots & 0 & 0 & \cdots & 0 \\ \vdots & \ddots & \vdots & \vdots & \vdots & \vdots \\ 0 & \cdots & \sigma_n & 0 & \cdots & 0 \end{pmatrix} \cdot \begin{pmatrix} V_{11} & \cdots & V_{1n} \\ \vdots & \ddots & \vdots \\ V_{n1} & \cdots & V_{nn} \end{pmatrix}^{*}$$

where V* is the conjugate transpose matrix of V and the number of singular values of S is equal to the rank of X.

Figure 4:
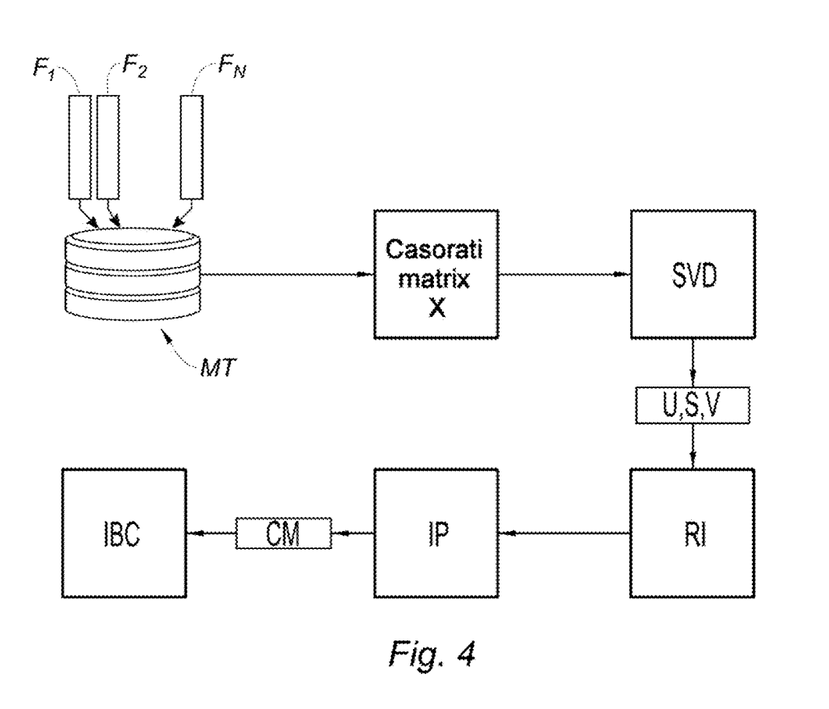
FIG. 4, an illustration of the singular-value-decomposition algorithm.

When the SVD method is applied to image processing, the lowest singular values are associated with noise, and most of the energy of the image is compacted into the singular values of high value. In the case of the invention, SVD spatio-temporal filtering is used to separate undesirable low-frequency components from the high-frequency components associated with the cloud of cavitation bubbles via a judicious choice of the singular vectors. This is illustrated in FIG. 4.

A set of N "passive" images $F_1, F_2, \ldots F_N$, associated with respective therapy pulses and reconstructed using a parallel beamforming algorithm, each image being of ($n_x$, $n_y$) size and stored in a buffer memory MT, is considered. These data may be rearranged into a two-dimensional spatio-temporal matrix X of ($n_x \cdot n_y$, N) size, called the Casorati matrix. The singular value decomposition of this matrix (reference SVD in FIG. 4) consists in finding the temporal and spatial singular vectors forming the columns of the matrices U and V, respectively, and the corresponding singular values forming the matrix S. Advantageously, these vectors are ordered by decreasing energy.

The actual spatio-temporal filtering consists in reconstructing the image using solely the singular vectors that describe the cloud of bubbles. It is assumed that these vectors are associated with contiguous singular values of indices comprised between p and q>p. The filtered image $X_{BC}$ is therefore given by:

$$X_{BC}(n_x \times n_z, N) = \sum_{i=p}^{q} \sigma_i U_i V_i^T \quad \text{(Eq. 2)}$$

(reference RI in FIG. 4).

The terms of the filtered Casorati matrix $X_{BC}(n_x n_z, N)$ may be rearranged into a three-dimensional matrix $X_{BC}(n_x, n_y, N)$, and it is possible to compute its power integral, or cavitation map CM, which allows the most energetic regions of the image to be located:

$$CM(n_x, n_z) = \int |X_{BC}(n_x, n_z, N)|^2 \quad \text{(Eq. 3)}$$

(reference IP in FIG. 4).

It is important to note that N images give a single cavitation map; in other words, the acquisition rate is divided by N.

The cavitation map is used as the final image of the cloud of cavitation bubbles, which image is intended to be superposed on the image of the tissues that is obtained by active echography (reference IBC in FIG. 4). False colors may be used to represent the values of the map CM.

The spatial resolution of the map CM is limited by the length of the ultrasonic pulses in the direction of propagation, which is given by the product of their duration multiplied by their propagation speed. Thus, pulses that are as short as possible and, at the shortest, with a duration equal to one cycle of the ultrasonic wave, will preferably be used. By duration of the pulses, what is meant is the duration (i.e. the temporal support) of the electronic pulses used to control the therapy transducer, the finite bandwidth of the latter inevitably leading to an elongation of the ultrasonic pulses actually emitted. In practice, the duration of the pulses is not chosen solely with regard to the imaging resolution but also, or even above all, depending on the requirements of the therapeutic protocol.

The choice of the optimal values of the parameters N, p and q depends on the specific application in question. The inventors have observed that the echo signals originating from tissues (that it is desired to eliminate) are mainly concentrated in the first singular vector, the N−1 following singular vectors mainly containing the contributions of the cavitation bubbles (that it is desired to isolate). Therefore, p may be set equal to 2 (p=2) and q set equal to N (q=N). As regards the parameter N, the inventors have observed that the contrast-to-noise ratio (defined below) rapidly increases with N provided that the value of this parameter remains lower than or equal to about 10, then tends to plateau. Below, three cases have been considered: N=6; N=10 and N=14.

The contrast-to-noise ratio, which defines the quality of the images (more precisely, of the cavitation maps) is given by:

$$CNR = \frac{\langle CM(n_x, n_z) \rangle_1 - \langle CM(n_x, n_z) \rangle_2}{\sqrt{\sigma_1 \sigma_2}} \quad \text{(Eq. 4)}$$

where $\langle \ \rangle_i$ designates a spatial average and $\sigma_i$ the standard deviation in these two regions in the region i (i=1: cloud of bubbles; i=2: background). The regions 1 and 2 will be identified manually.

As a variant, the spatio-temporal filtering step may be implemented before the beam formation. In this case, the spatial component of the filtering relates to the elements of the imaging probe.

In order to test the invention, a phantom was prepared with a volume of 1.75 L of water and 8% polyvinyl alcohol (PVA). Ultrasound scatterers were added using 1% cellulose (Sigmacell, 20 μm, USA). Tap water was heated to 90° C. using a laboratory heating apparatus and the required volume was poured into a beaker with a magnetic steering pivot pin. The PVA was then dissolved in water. The mixture was cooled to 40° C., cellulose was added and the solution was poured into a square container made of plastic and placed in the freezer for 8 hours. The phantom was then thawed, then put back in the freezer for 8 hours. At the end of the procedure, the phantom was de-molded and placed in a tank of water for the cavitation experiments.

The assembly of transducers of an apparatus according to the invention was attached to a two-axis stage (PI, Micos, Germany) and placed inside the tank of water containing the phantom. To model a physiological movement of the region of the body to be treated, axial and lateral movements of the transducers were induced with different speeds, a top speed of 10 mm/s with an amplitude of movement of 10 mm for the axial movement and a top speed of 10 mm/s with an amplitude of movement of 8 mm for the lateral movement.

Figure 5:
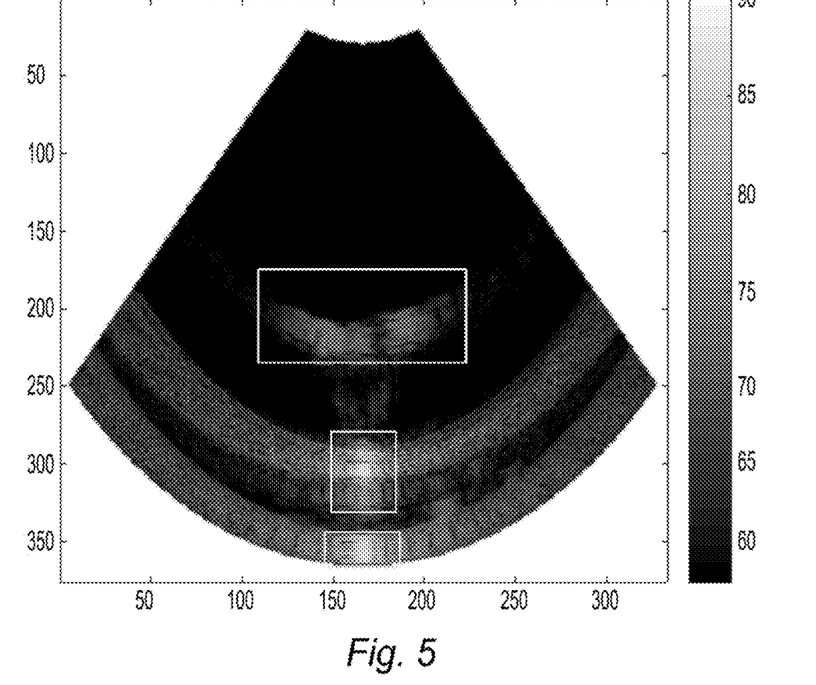
FIG. 5, a cavitation image obtained using an apparatus according to one embodiment of the invention.

FIG. 5 shows an image of the cloud of cavitation bubbles obtained in this way. The cloud is identified by a white box. Artefacts are present above and below the image; they are most likely due to reflections of the ultrasonic pulses from the water-phantom interfaces.

The contrast-to-noise ratio CNR of the "passive" images of the cloud of cavitation bubbles obtained for N=6, 10 and 14 (again with p=2 and q=N) was measured, both under static conditions and with the transducers moving. Similar measurements were also performed using active imaging techniques. The inventors have observed that active imaging of the cavitation bubbles gives results that were slightly better than passive imaging under static conditions, but that the converse is true with the transducers moving. This validates the use of a passive method in the invention.

Figure 6:
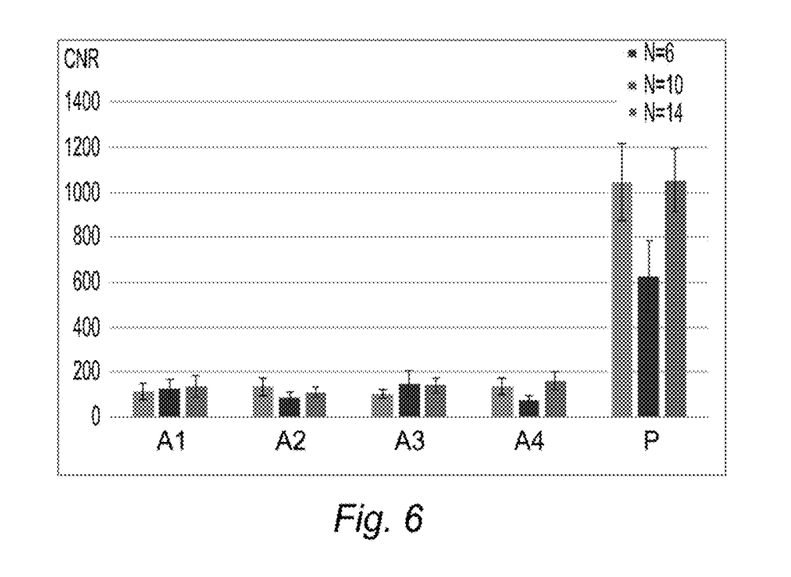
FIG. 6, a graph illustrating a technical effect of the invention.

The results obtained with the transducers moving are illustrated in FIG. 6, in which the reference P designates the CNR of the passive images and A1-A5 designate that of the images obtained using active methods:
   A1: active imaging obtained with emission of a plane ultrasound wave after each therapy pulse.
   A2: ultra-rapid sequence with a block of eleven emissions of directed divergent waves after each therapy pulse, combined into a single image.

A3: ultra-rapid sequence with a block of ten emissions of divergent waves (without combination) after each therapy pulse, this giving a block of ten images every 10 milliseconds.

A4: ultra-rapid sequence with a block of one-hundred ten emissions of directed divergent waves distributed over three therapy pulses, which are combined into ten images. Each image is the result of the combination of eleven oriented divergent waves. This sequence gives a block of ten images about every 35 milliseconds.

In fact, what is observed is that the movements of the transducers induce a very substantial degradation in the performance of the active imaging techniques (one order of magnitude), whereas the CNR of the images obtained according to the invention decreases only by a factor of about two. This may be explained in the following way. When the region to be treated is (or, equivalently, the transducers are) moving, the reflections from the tissues contain high-frequency incoherent spatio-temporal components that interfere with the useful components reflected from the cavitation bubbles. However, in active imaging, tissues in the entirety of the observation region are exposed to ultrasound and therefore generate echoes. In contrast, in passive imaging, focused ultrasound is used, this decreasing the parasitic contribution due to the tissues.

References:

[1] B. Arnal, J. Baranger, C. Demene, M. Tanter and M. Pernot (2016). In vivo real-time cavitation imaging in moving organs. Phys Med Biol. 2017 Feb. 7; 62(3):843-857.

[2] Christian Coviello, Richard Kozick, James Choi, Miklós Gyöngy, Carl Jensen, Penny Probert Smith, and Constantin-C. Coussios (2015). Passive acoustic mapping utilizing optimal beamforming in ultrasound therapy monitoring. The Journal of the Acoustical Society of America 137, 2573.

[3] Kevin J. Haworth, Kenneth B. Bader, Kyle T. Rich, Christy K. Holland, Member and T. Douglas Mast (2017). Quantitative Frequency-Domain Passive Cavitation Imaging. IEEE transactions on ultrasonics, ferroelectrics, and frequency control, vol. 64, no. 1.

[4] Bader Kenneth, Haworth Kevin, D. Maxwell Adam, Holland Christy (2017). Post Hoc Analysis of Passive Cavitation Imaging for Classification of Histotripsy-Induced Liquefaction in Vitro. IEEE Transactions on Medical Imaging.

[5] P. Boulos, F. Varray, A. Poizat, J. C. Bera, C. Cachard (2015). Passive cavitation imaging using an open ultrasonic system and time reversal reconstruction. 22ème Congrès Français de Mécanique Lyon.

The invention claimed is:

1. An apparatus for providing treatment with ultrasound, the apparatus comprising:
a therapy ultrasound transducer (ATA) configured for generating focused ultrasonic waves;
an imaging ultrasound transducer (UID) distinct from but associated with the therapy ultrasound transducer; and
an electronic system configured to:
control the therapy ultrasound transducer so as to emit a pulse train of ultrasonic waves of energy with a duration suitable for causing generation of a cloud of cavitation bubbles (BC) in a focal spot (TF) of the transducer when said focal spot is positioned inside a region to be treated of a human or animal body;
control the imaging ultrasound transducer so as to emit, between two ultrasonic-wave pulses emitted by the therapy ultrasound transducer, ultrasonic waves that are directed toward the region to be treated to acquire echoes of said ultrasonic waves and to process the echoes to reconstruct at least one image of the region to be treated;
acquire a plurality of echo signals of N>1 ultrasonic-wave pulses emitted by the therapy ultrasound transducer, said signals being captured by the imaging ultrasound transducer;
process said echo signals of the N>1 ultrasonic-wave pulses emitted by the therapy ultrasound transducer using a beamforming algorithm, so as to form respective echo images, and using spatio-temporal filtering allowing components of said echo images that are representative of a backscatter of the ultrasonic-wave pulses from the cavitation bubbles to be extracted, separating them from components representative of a backscatter from tissues of the region to be treated, so as to reconstruct an image (IBC) of the cloud of cavitation bubbles; and
display, superposed on said image of the region to be treated, said image of the cloud of cavitation bubbles;
wherein processing said echo signal comprises, during the reconstruction of the image of the cloud of cavitation bubbles, introducing a compensation for a difference between the propagation time of the ultrasonic waves from the therapy ultrasound transducer and the focal spot, and the propagation time of the ultrasonic waves from the focal spot and the imaging ultrasound transducer.

2. The apparatus for providing treatment by ultrasound as claimed in claim 1, wherein said electronic system is configured to control the therapy ultrasound transducer so as to emit a train of ultrasonic-wave pulses with a duration between 0.1 µs and 50 µs.

3. The apparatus for providing treatment by ultrasound as claimed in claim 1, wherein N is between 2 and 10,000.

4. The apparatus for providing treatment by ultrasound as claimed in claim 1, wherein said electronic system is configured to reconstruct the image of the cloud of cavitation bubbles by means of a parallel beamforming algorithm.

5. The apparatus for providing treatment by ultrasound as claimed in claim 1, wherein the electronic system and the therapy ultrasound transducer are configured to emit ultrasonic-wave pulses with a duration between 0.1 µs and 50 µs, with a central frequency comprised between 100 kHz and 5 MHz, at a repetition rate comprised between 1 and 1000 Hz.

6. The apparatus for providing treatment by ultrasound as claimed in claim 1, wherein the electronic system and the imaging ultrasound transducer are configured to emit ultrasonic-wave pulses having a central frequency comprised between 2 and 15 MHz.

7. The apparatus for providing treatment by ultrasound as claimed in claim 1, wherein the electronic system is configured to perform said spatio-temporal filtering using singular value decomposition.

8. The apparatus for providing treatment by ultrasound as claimed in claim 1, wherein the therapy ultrasound transducer and the imaging ultrasound transducer are arranged coaxially.

9. The apparatus for providing treatment by ultrasound as claimed in claim 1, further comprising means for moving the focal spot of the ultrasonic-wave pulses emitted by the therapy ultrasound transducer in the treatment region.

10. The apparatus for providing treatment by ultrasound as claimed in claim 1, wherein the electronic system is also configured to adjust a power level of the ultrasonic-wave pulses emitted by the therapy ultrasound transducer depending on the image of the cloud of cavitation bubbles.

11. A method for providing treatment with ultrasound using an apparatus comprising:
- a therapy ultrasound transducer (ATA) configured for generating focused ultrasonic waves; and
- an imaging ultrasound transducer (UID) distinct from but associated with the therapy ultrasound transducer;

the method comprising:
- using the therapy ultrasound transducer to emit a pulse train of ultrasonic waves of energy with a duration suitable for causing generation of a cloud of cavitation bubbles (BC) in a focal spot (TF) of the transducer when said focal spot is positioned inside a region to be treated of a human or animal body;
- using the imaging ultrasound transducer to emit, between two ultrasonic-wave pulses emitted by the therapy ultrasound transducer, ultrasonic waves that are directed toward the region to be treated to acquire echoes of said ultrasonic waves and to process the echoes to reconstruct at least one image of the region to be treated;
- acquiring a plurality of echo signals of N>1 ultrasonic-wave pulses emitted by the therapy ultrasound transducer, said signals being captured by the imaging ultrasound transducer;
- processing said echo signals of the N≥1 ultrasonic-wave pulses emitted by the therapy ultrasound transducer using a beamforming algorithm, so as to form respective echo images, and using spatio-temporal filtering allowing components of said echo images that are representative of a backscatter of the ultrasonic-wave pulses from the cavitation bubbles to be extracted, separating them from components representative of a backscatter from tissues of the region to be treated, so as to reconstruct an image (IBC) of the cloud of cavitation bubbles; and
- displaying, superposed on said image of the region to be treated, said image of the cloud of cavitation bubbles;
- wherein processing said echo signal comprises, during the reconstruction of the image of the cloud of cavitation bubbles, introducing a compensation for a difference between the propagation time of the ultrasonic waves from the therapy ultrasound transducer and the focal spot, and the propagation time of the ultrasonic waves from the focal spot and the imaging ultrasound transducer.

12. The method for providing treatment with ultrasound as claimed in claim 11, further comprising controlling the therapy ultrasound transducer to emit a train of ultrasonic-wave pulses with a duration between 0.1 µs and 50 µs.

13. The method for providing treatment by ultrasound as claimed in claim 11, wherein N is between 2 and 10,000.

14. The method for providing treatment by ultrasound as claimed in claim 11, further comprising reconstructing the image of the cloud of cavitation bubbles by means of a parallel beamforming algorithm.

15. The method for providing treatment by ultrasound as claimed in claim 11, further comprising using the therapy ultrasound transducer to emit ultrasonic-wave pulses with a duration between 0.1 µs and 50 µs, with a central frequency comprised between 100 kHz and 5 MHz, at a repetition rate comprised between 1 and 1000 Hz.

16. The method for providing treatment by ultrasound as claimed in claim 11, further comprising using the imaging ultrasound transducer to emit ultrasonic-wave pulses having a central frequency comprised between 2 and 15 MHz.

17. The method for providing treatment by ultrasound as claimed in claim 11, further comprising performing said spatio-temporal filtering using singular value decomposition.

18. The method for providing treatment by ultrasound as claimed in claim 11, wherein the therapy ultrasound transducer and the imaging ultrasound transducer are arranged coaxially.

19. The method for providing treatment by ultrasound as claimed in claim 11, further comprising moving the focal spot of the ultrasonic-wave pulses emitted by the therapy ultrasound transducer in the treatment region.

20. The method for providing treatment by ultrasound as claimed in claim 11, further comprising adjusting a power level of the ultrasonic-wave pulses emitted by the therapy ultrasound transducer depending on the image of the cloud of cavitation bubbles.

* * * * *